United States Patent [19]

Bruno

[11] Patent Number: 5,172,808
[45] Date of Patent: Dec. 22, 1992

[54] DEVICE FOR SAFELY TRANSPORTING ONE OR MORE HYPODERMIC NEEDLES OR THE LIKE FROM POINT OF USE TO POINT OF ULTIMATE DISPOSAL

[76] Inventor: John Bruno, 77-83 Second Ave., Paterson, N.J. 07514

[21] Appl. No.: 353,240

[22] Filed: May 17, 1989

Related U.S. Application Data

[63] Continuation-in-part of Ser. No. 214,332, Jul. 1, 1988, abandoned.

[51] Int. Cl.$^5$ ............................................. B65D 83/10
[52] U.S. Cl. ................................ 206/366; 206/370; 206/364; 206/367; 220/908; 220/603
[58] Field of Search ............... 206/364, 365, 366, 367, 206/370, 438, 569, 570, 571, 574; 220/1 T, 68, 908, 603; 604/192, 197, 263

[56] References Cited

U.S. PATENT DOCUMENTS

| | | | |
|---|---|---|---|
| 656,914 | 8/1900 | Walsh | 206/367 |
| 764,564 | 7/1904 | Dreyer | 604/192 |
| 1,580,104 | 4/1926 | Hasselmann | 206/366 |
| 1,581,341 | 4/1926 | Guinness | 206/365 |
| 1,686,651 | 10/1928 | Close | 220/603 |
| 1,711,594 | 5/1929 | Gillespie | 206/365 |
| 2,264,313 | 12/1941 | Humphrey | 206/366 |
| 2,346,725 | 4/1944 | Butzke | 206/366 |
| 2,400,722 | 5/1946 | Swan | 206/43 |
| 2,417,626 | 3/1947 | Blocher | 206/365 |
| 2,421,495 | 6/1947 | Green | 206/365 |
| 2,492,326 | 12/1949 | Scotti | 206/364 |
| 2,929,510 | 3/1960 | Penn | 206/366 |
| 2,932,423 | 4/1960 | Baumgartner | 220/603 |
| 3,098,482 | 7/1963 | O'Sullivan | 128/220 |
| 3,270,743 | 9/1966 | Gingras | 128/215 |
| 3,331,499 | 7/1967 | Jost | 206/367 |
| 3,380,489 | 4/1968 | Harautuneian | 206/364 |
| 3,481,462 | 12/1969 | Chapel | 206/564 |
| 3,637,072 | 1/1972 | Narusawa et al. | 206/365 |
| 3,783,996 | 1/1974 | Gerard et al. | 206/364 |
| 3,819,039 | 6/1974 | Erickson | 206/388 |
| 3,876,067 | 4/1975 | Schwarz | 206/205 |
| 3,893,608 | 7/1975 | Koenig | 225/1 |
| 4,050,894 | 9/1977 | Genis | 206/364 |
| 4,214,659 | 7/1980 | Jaeschke et al. | 206/365 |
| 4,623,336 | 11/1986 | Pedicano et al. | 604/192 |
| 4,629,453 | 12/1986 | Cooper | 604/192 |
| 4,735,617 | 4/1988 | Nelson et al. | 604/192 |
| 4,740,204 | 4/1988 | Masters et al. | 604/192 |
| 4,801,013 | 1/1989 | Bruno | 206/366 |
| 4,804,090 | 2/1989 | Schuh et al. | 206/366 |
| 4,813,538 | 3/1989 | Blackman | 206/366 |
| 4,816,307 | 3/1989 | Honeycutt | 206/366 |
| 4,936,449 | 1/1990 | Conard et al. | 206/366 |
| 4,969,554 | 11/1990 | Sawaya | 206/370 |

FOREIGN PATENT DOCUMENTS

| | | | |
|---|---|---|---|
| 366105 | 12/1922 | Fed. Rep. of Germany | 206/364 |
| 258857 | 6/1928 | Italy | 206/365 |

Primary Examiner—David T. Fidei
Attorney, Agent, or Firm—Morgan & Finnegan

[57] ABSTRACT

A storage/carrying device for safely and conveniently transporting used needle and syringe devices for medication purposes and blood collection procedures, and, additionally, to safely transport such implements to ultimate disposal after use, which includes a generally tubular container having a needle engaging insert fixedly positioned at the bottom thereof. The needle engaging insert is adapted to receive and fixedly engage the needle portion of a used needle/syringe device to substantially reduce the potential for the syringe to roll within the container during transport, and substantially reduce the risk of the needle/syringe dislodging from the container in the event the container is inadvertently dropped or inverted during use. The tubular container preferably is weighted at its bottom and can be conveniently dimensioned to be carried on the person of the user independent of any storage/carrying device.

10 Claims, 4 Drawing Sheets

DEVICE FOR SAFELY TRANSPORTING ONE OR MORE HYPODERMIC NEEDLES OR THE LIKE FROM POINT OF USE TO POINT OF ULTIMATE DISPOSAL

CROSS-REFERENCE TO RELATED APPLICATION

This application is a continuation-in-part of Applicant's co-pending application Ser. No. 07/214,332 filed Jul. 1, 1988, now abandoned.

BACKGROUND AND OBJECTS OF THE INVENTION

The present invention relates generally to devices which facilitate bedside infection control in hospitals, and, more particularly, to a device which provides for safe and convenient transport of a used hypodermic needle or the like from a patient's bedside after use in, for example, administering medication or collecting blood to the point of ultimate disposal of such needles.

With the widespread use of disposable medical implements, particularly hypodermic needles, a definite need has developed for ways to safely and conveniently handle and transport such implements after use, so that disposal can be effected without risk of exposing any person handling the used implements to injury, infection or disease by puncture or contact with a used needle or syringe. The tragic outbreak of the highly contagious AIDS disease has dramatically hightened the need for safer handling, storage and disposal of such implements.

In today's hospitals, a wide variety of disposable needle and syringe devices are routinely used to administer medication by injection and intravenous ("I.V.") procedures, and for intravenous blood collection. Once an injection is given, a blood sample drawn, or an I.V. needle removed from a patient, both the needle and/or syringe used in the procedure may be contaminated and must be disposed of in a safe manner.

It had once been common practice to break or cut the needle after use before transport to ultimate disposal in order to eliminate the sharp end point so as to reduce the risk of puncture, scratching or other injury which might result from handling. However, the very act of breaking or cutting the needles gives rise to a substantial danger that accidental puncture might occur during the breaking or cutting operations, thus exposing the holder to possible injury and, further, to possible infection or disease as a result of such puncture. In addition, residual medication or blood in the needle or the syringe can splatter onto the person or his clothes, and, potentially harmful fumes from the residual medication could be inhaled as a result of the so-called aerosol effect. Furthermore, the blades of the cutting tool are now recognized as a breeding ground for germs, bacteria and other disease-causing micro-organisms to which an unsuspecting person cutting the needle could be unnecessarily exposed.

Recently, an even greater danger has been recognized in connection with the handling and disposal of used needles as well as other sharp medical implements. It is now recognized that certain diseases, most notably Hepatitis B, can be transmitted by covert percutaneous—i.e., by merely contacting the contaminated needle or implement.

While the used needle portion presents the most significant risk of injury or infection through accidental puncture or scratching of a person's skin, the used syringe part may also present a risk of infection. For example, a used syringe can contain residual blood or medication which, if exposed to a person's skin, may be absorbed topically (particularly if a cut or break in the skin is present) and may cause a serious internal infection or other reaction. Thus, even where such a needle removal and storage device is employed, the used syringe will still require independent, safe disposal.

As a result of the foregoing dangers, it is preferred current practice to dispose of such devices in-tact, without dismantling them. However, in disposing of the whole hypodermic needle and syringe, the used needle has sometimes been recapped before disposal with the same protective sheath that was used during shipment from the manufacturer. The resheathing was intended to prevent possible injury while a person carries the needle to a suitable disposal unit. This practice itself, however, can result in accidental puncture or contact while the needle point is being resheathed. Because of this danger it is now recommended by the Center For Disease Control ("C.D.C.") that needles not be resheathed after use.

In this regard, the C.D.C. has been strongly urging hospitals to provide in-room receptacles for disposal of used needle/syringe assemblies in-tact, without recapping the needle. While such disposal devices have been generally satisfactory, they may still have a few shortcomings. In-room disposal devices can be costly and require permanent installation in a patient's room. Moreover, in-room receptacles may not eliminate the inherent risk of contaminating contact or accidental puncture associated with the manual transport of an exposed used needle/syringe assembly even a short distance from the patient's bedside.

Most importantly, the nurse, as a practical matter, almost always has important duties to perform immediately after giving an injection or drawing blood (such as treating the injected area, covering the exposed patient, etc.) which makes walking to a receptacle to dispose of a used needle a lesser priority, and thereby increases the risk that an exposed needle will be left on a nearby table or even on the patient's bed. This could be particularly hazardous in the case of medical personnel who leave used needle/syringe assemblies unattended in a psychiatric patient's room for even a few seconds while attending to other duties within or without the patient's room.

Additionally, there may be instances where a disposal device for the whole needle/syringe assembly is not desired. For example, in emergency rooms, the urgency of a particular emergency situation may not permit time to seek out an appropriate disposal unit for the used needle/syringe assembly In the absence of an immediately available disposal device it is likely that the used needle could be left lying unattended and unsecured, or an attempt might be made to resheath the needle. In either event, there are substantial risks of accidental puncture by or contact with contaminated needles Accordingly, it is an object of the present invention to provide a new transport device for temporarily holding a used needle or other "sharps" implements in a safe manner until its ultimate disposal.

It is also an object of the invention to provide a new sharps transport device for conveniently and safely storing and transporting used hypodermic needles and syringes, as well as butterfly or other intravenous-type needle assemblies, to ultimate disposal without exposing the person handling the device to the risk of injury, infection or disease by puncture or contact with the used needle or syringe.

It is a further object of the present invention to provide a new sharps transport device for conveniently and safely securing, for transport, used needle/syringe assemblies to ultimate disposal, in-tact, thus eliminating both the need for potentially costly in-room disposal receptacles, and/or the risk of accidental puncture or contact with a contaminated needle inherent during manual transport to such disposal devices even though there may only be a short distance to the disposal device. In addition, the sharps transport device of the present invention provides means whereby a used needle can be rendered virtually harmless immediately after use.

It is yet another object of the present invention to provide a new sharps transport device for storing and transporting used needles and syringes to ultimate disposal which is compact in size so as to be easily locked inside a standard hospital medication cart when unattended, thus obviating the risks caused by leaving unattended receptacles in patient's rooms.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a re-usable, open-ended container for securing and transporting one or more used needle/syringe assemblies in-tact to an ultimate disposal facility. As preferably embodied, the container includes a needle-pierceable insert at the bottom thereof made from a sponge-like foam or rubber or plastic-type material into which the needle portions of the used devices can be inserted to ensure that the needle points are secured against possible puncture or contact during transport, and that any residual blood or medication in the needles can drain and be absorbed.

Also as preferably embodied, the container is weighted, preferably at its bottom, to provide upright stability and thereby enable, for example, a person who must give an injection or take a blood sample to place the container on a flat surface and easily insert a used needle/syringe assembly thereinto with one hand with little or no risk of tipping the container over. Advantageously, the container is provided with a tubular sleeve member formed with an open end and a closed end. The sleeve is proportioned to slidably fit over the top of the container and frictionally engage the container sidewall to securely enclose the used needle/syringe assemblies for transport to disposal. The sleeve is also slideably engagable with the container while in use.

According to one embodiment, the weight in the container is provided by disposing a heavy weight at the bottom of the container under the sponge-like member. The weight may be a metal blank or a nut proportioned to fit within the container, or it may be a ceramic magnet which has the added advantage of providing supplemental holding power when the container is placed on a metal surface. According to another preferred embodiment, the weight in the container is provided by pouring a hardenable composition into the container and allowing it to harden with the sponge-like material on top of it. Advantageously, the hardenable material can be a cement-like mixture which hardens upon setting to a relatively heavy bottom weight for the device.

Depending on the hardenable composition selected, the sponge-like material may become automatically adhered as the composition hardens. Alternatively, the sponge-like member can be adhered by glue or other appropriate adhesive means or it may simply be a friction fit within the housing. Also advantageously, the sponge-like material can be saturated with a disinfectant and/or deodorant to prevent any accumulation of germs and/or odors in the container.

It will be appreciated by those skilled in the art that the tubular container of the present invention is particularly useful for situations wherein it is desirable for the user to keep used needle/syringe asemblies on his or her person—e.g., while attending to a psychiatric patient who may harm himself or anyone else present in his room with an unattended exposed needle. The invention provides a readily available device which safely encapsulates the used needle portion(s) without risking the possibility of puncture that would be caused by re-sheathing yet gives the user flexibility as to when the used needle is actually placed in an ultimate disposal device.

It will be further appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

DETAILED DESCRIPTION OF PREFERRED EMBODIMENT

Figure 1:
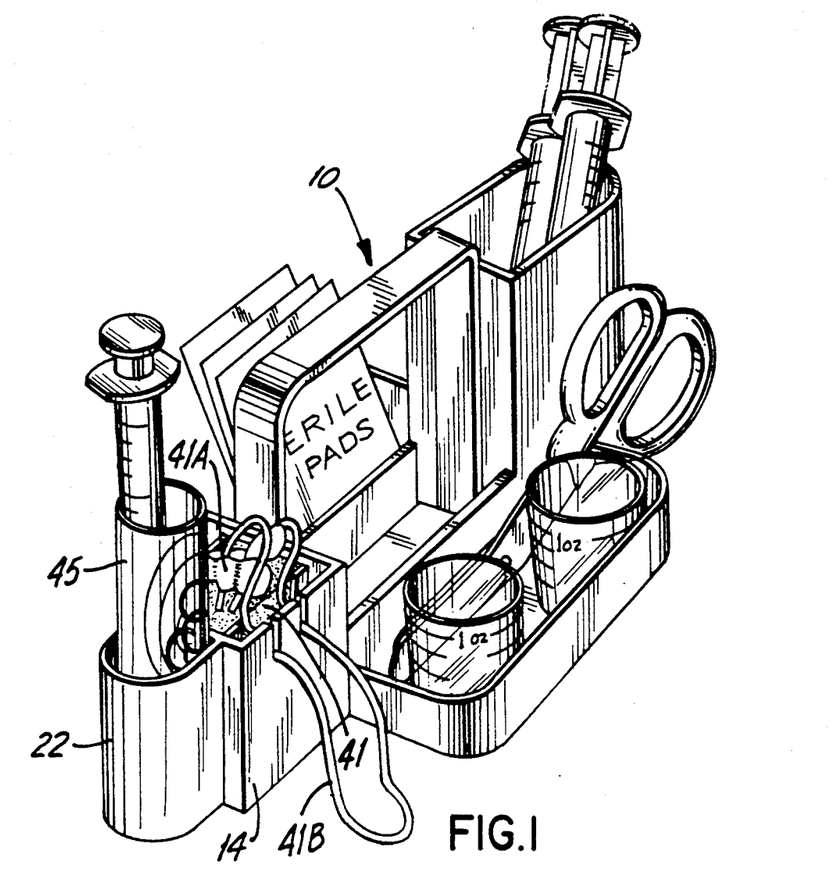
FIG. 1 is a perspective view of a storage/carrying device with an embodiment of a sharps transport device according to the present invention for transporting used needle/syringe assemblies to the place of ultimate disposal.

Referring now to the accompanying drawings, wherein like reference characters refer to like parts throughout the various views, FIG. 1 shows a preferred embodiment of medical supply/storage/carrying device (indicated generally at 10), having a used-needle transport device according to the present invention incorporated therein. For ease of disclosure, applicant hereby incorporates by reference herein, the disclosure of its earlier filed, co-pending application, Ser. No. 07/214,332, filed Jul. 1, 1988. In view of the foregoing incorporation by reference, a detailed element-by-element description of the carrying tray will not be necessary. Rather, it will be sufficient to make brief mention of only certain features of the carrying device.

Referring then to FIG. 1, the carrying device includes transport well 14 which is provided with a generally rectangular needle engaging element 41 adapted to fixedly engage the needle portions of used I.V. needle assemblies (shown as 41a) for transport to disposal. Element 41 is fabricated from a foam-type material which is resilient, yet substantially rigid enough, such that the needle portion of a used I.V. needle assembly can be easily and securely inserted to "stuck" into the top of element 41 for transport to disposal, yet easily removed from the element at the disposal site. As here embodied, element 41 is dimensioned to accommodate the needle portions of at least four intravenous-type needle assemblies, the tubing connections (shown as 41b) of which are engagable within the two pairs of engaging slots formed in sidewalls of the transport, as described in my aforesaid application.

In addition, as preferably embodied, the carrying device is provided with an open-ended, tubular container 45 adapted to store and carry used needle/syringe assemblies to disposal, in-tact, without having to disassemble the needles from the syringes. As described in my aforesaid application container 45, in and of itself, is a transport device and is adapted to be removably received within extension well 22 of the carrying device.

Figure 2:
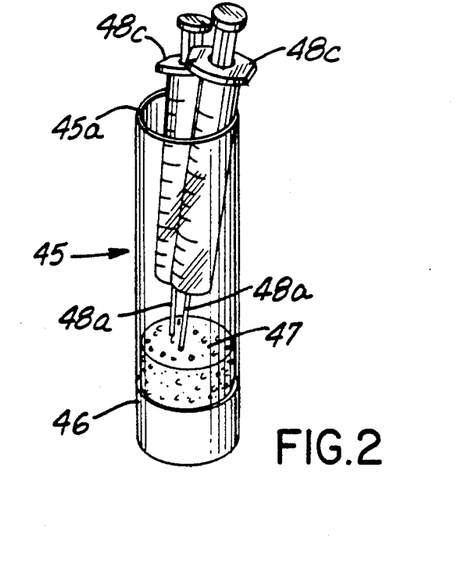
FIG. 2 is a front isometric view of the transport device shown in FIG. 1 with used needle/syringe assemblies therein.

As shown in FIG. 2, container 45 has a tubular sidewall 45a formed from a plastic material adapted for frictional engagement with extension well 22. As here embodied, the bottom of the container is provided with a hard, hollow plastic plug 46 for enhanced structural stability, but it can be fabricated as a unitary, tubular piece if desired. Container 45 (and thus extension transport well 22) can be dimensioned to accommodate any size needle/syringe assembly or a plurality thereof, and, preferably, should have an interior sidewall height such that the finger grips (shown as 48c) of the syringes (shown as 48b) are sufficiently exposed above the sidewall of the container to permit easy removal of a needle/syringe assembly for disposal, while reducing the risk of potentially contaminating contact with the interior of the sidewall.

According to an exemplary embodiment, the container 45 is dimensioned to an interior height of approximately 3½ inches and an interior diameter of approximately 1⅛ inches, which will safely and comfortably accommodate four 3 millileter syringes. For use with a 60 millileter syringe, the interior diameter of the container should preferably be approximately 1⅜ inches.

Advantageously, the interior of the container is provided with a needle engaging insert 47 into which the needle portions (shown as 48a) of used needle/syringe assemblies (shown as 48) can be tightly inserted. As here embodied, insert 47 is dimensioned to essentially the interior diameter of the container and to a height of approximately one inch. Preferably, element 47 is fabricated from a sponge rubber or plastic-type material to ensure a tight engagement with the needle upon insertion thereinto. Further, insert 47 is permanently affixed within container 45 near the container floor, preferably via a hot glue-type compound, to ensure that the insert will not be inadvertently pulled out of the container in response to the removal of a needle therefrom.

In use, a needle/syringe assembly ready for disposal is placed in container 45 (which has been tightly inserted into extension well member 22) such that the exposed needle is tightly stuck through insert 47. The tubular sidewall of the container surrounds the body of the syringe with the fingergrips thereof exposed above the sidewall. Any residual blood or medication remaining in the needle can drain into and be absorbed by insert 47. Advantageously, because of the tight engagement between the needle and insert 47, and the relatively small area for movement of the syringe provided by the diameter of the container, the potential for the needle/syringe assembly to roll about the sidewall of the container during transport to disposal, and thus the attendant sense of uneasiness about transporting the device under such circumstances, will be substantially reduced. Further, the tight engagement of the needle with the material of insert 47 will substantially reduce the risk of the needle/syringe assembly falling out of the container in the event the container is inadvertently tipped over or dropped during use.

When the container is filled to capacity with used needle/syringe assemblies it can be carried via storage/carrying device 10 (or, as described hereafter, by itself on a med-cart) to the disposal site. There, the used devices can be removed from the container and put in the disposal unit. The container can then be reused for further procedures. Each container can then be reused for further procedures. Each container 45 should be reused until the gripping power of insert 47 is substantially reduced, and thereby, the risk of a used needle/syringe assembly falling out of the container substantially increased. However, it is preferred that each container be disposed of after a 2 to 3 week period to guard against a potential undue build-up of contamination within the container.

Figures 3A, 3B, 3C:
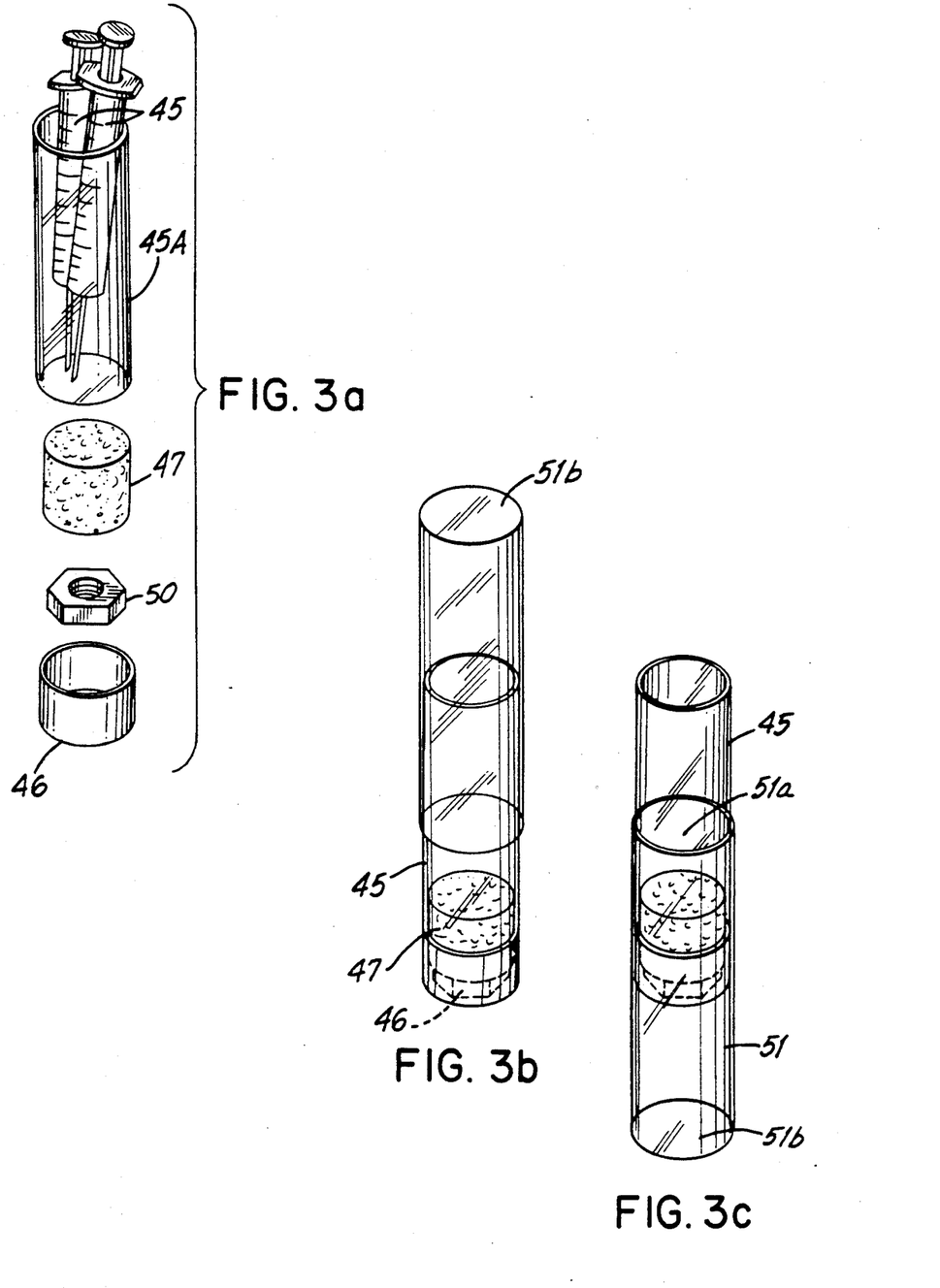
FIG. 3a is an exploded isometric view of the device shown in FIG. 2.
FIGS. 3b and 3c show alternate ways of forming a sharps transport device according to the present invention.

According to another aspect of the invention, container 45 can be adapted for use independent of storage/carrying device 10. As illustrated in FIG. 3a, container 45 as hereinbefore described is additionally provided with a metal insert 50 (shown as a metal nut) securely sandwiched via a hot-glue compound between the bottom of needle engaging insert 47 and the bottom of hollow plastic plug 46. Insert 50 should be of a sufficient weight to stabilize the container when placed on a flat surface so that the container will not tip over or lean when a used needle/syringe assembly is inserted thereinto. Preferably, insert 50 should weigh at least 1⅛ ounces, and should have a diameter essentially equal to the inside diameter of plug 46 so as to be snugly insertable therewithin. Advantageously, the added weight provided by insert 50 enables the user to place the container on a flat surface and insert the used needle/- syringe assembly thereinto quickly and easily with one hand, without fear that the container will tip over.

As shown in FIGS. 3b and 3c, container 45 is further provided with an elongated tubular sleeve 51 having an open end 51a and a closed end 51b. As here embodied, sleeve 51 can be slidably placed via open end 51a over outer sidewall 45a of the container at either end thereof, and is proportioned for a secure frictional engagement with the sidewall. Thus, the sleeve can be fit over the top of container 45 to cover the exposed finger grip portions of the used needle/syringe assemblies inserted into the container, or fit over the bottom of the container to secure the sleeve to the container while in use. Moreover, sleeve 51 is preferably elongated to cover a substantial portion of the container when slidably placed over either end so as to substantially reduce the risk of the sleeve falling off the container during use, yet expose a small portion of the container which can be grasped by the user to hold the container in place and thereby facilitate removal of the sleeve from the container. It will be recognized by those skilled in the art that the sleeve may be easily and securely affixed to either end of the container by means other than frictional engagement, for example, via reciprocating threads formed on the interior of open end 51a of the sleeve and the exterior of sidewall 45a of the container.

In use, a nurse or other medical person who must give an injection or draw a blood sample from a patient will remove sleeve 51 from the top of container 45, slidably secure it over the bottom end of the container, and place the container on a nearby flat surface. After performing the procedure, the nurse will simply place the used needle/syringe assembly within container 45 such that the needle end is securely stuck into insert 47, and then remove sleeve 51 from the bottom of the container and secure it back over the top of the container to completely cover the needle/syringe assembly. The nurse can then simply place the container in a uniform pocket and further attend to the patient, as well as to other patients. When container 45 is filled to capacity with used needle/syringe assemblies, the nurse can carry it to the disposal site, remove the sleeve from the top of the container, slide it over the container bottom, and remove the used devices for placement in the disposal unit. The container can then be reused as hereinbefore described.

It should be understood that the foregoing is not meant to exclude other embodiments which facilitate the objects of this aspect of the present invention. For example, insert 50 can be fashioned from a ceramic magnetic material and the bottom of plug 46 opened to expose the magnet to metallic surfaces onto which the container may be placed. As such, the magnetic attraction between the metal surface and the magnet will enhance the upright stability of the container. (It will be recognized that this embodiment is less preferred to use with non-metallic surfaces because of the relatively light weight of the magnet). Further, a heavier plug 46 can be provided which will serve to eliminate insert 50 altogether.

It will be appreciated by those skilled in the art that container 45, as preferably embodied, is particularly advantageous for use with psychiatric patients, from whom it is desirable to keep all items with which the patient could potentially inflict injury upon himself or others in or about his room. Also, the upright stability of container 45 provided by the foregoing aspect of the present invention facilitates compliance with the C.D.C. recommendation that medical personnel do not hold any type of sheath device in one hand while attempting to insert a needle thereinto with the other hand. As described above, container 45, which can be construed as a sheath, can be accessed with one hand to insert a used needle/syringe assembly thereinto.

Figure 4:
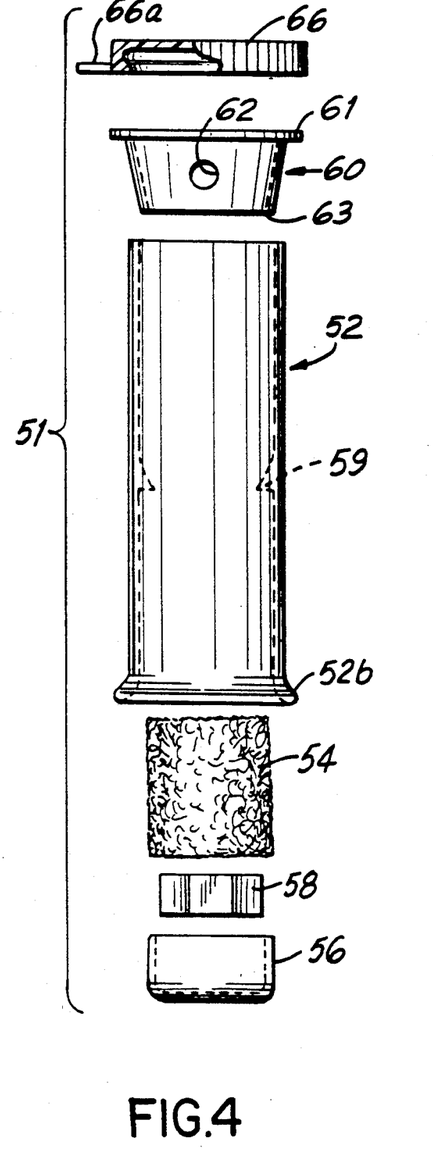
FIG. 4 shows an exploded view of an alternate embodiment of a sharps transport device according to the present invention.
Figure 5:
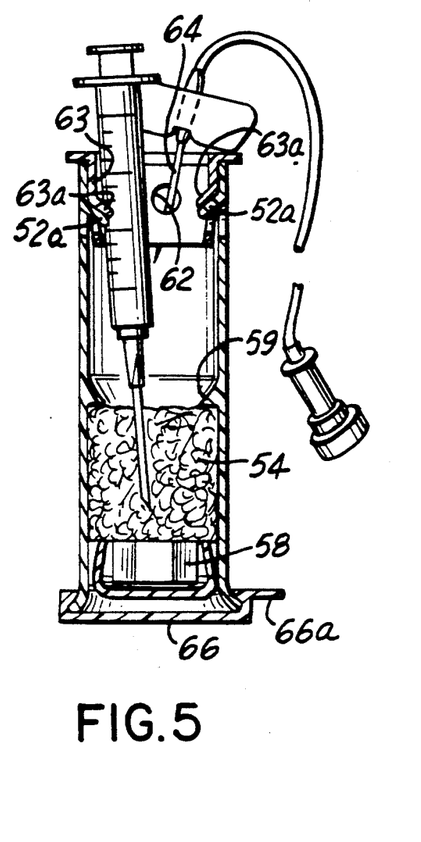
FIG. 5 is a sectional view of the assembled form of the embodiment shown in FIG. 4.

Turning now to FIGS. 4 and 5, there is illustrated an alternate embodiment of a sharps transport device according to the present invention. As here embodied, the transport device (indicated generally at 51) includes a hollow housing member (here in the form of a cylindrical sleeve or tube member 52) which is proportioned to receive a foam or sponge-like insert 54 similar to insert 47 described above. The bottom plug 56, similar to plug 46 described above. The bottom plug 56, similar to plug 46 described above, closes the bottom of housing 52 with weight 58 (similar to weight 50 described above) between the plug and insert 54. In addition, the weight 58 and insert 54 are preferably adhered together such as by hot glue (not shown.)

As preferably embodied, insert 54 is a sponge or foam-like material which can absorb liquids and has a memory. That is, when a needle is inserted into the insert and removed, the sponge-like material automatically returns substantially to its original configuration somewhat like inserting and removing the needle tip from a glass of water. A preferred material with such a memory is cross-link polyethylene. It will be understood by those skilled in the art that because of the memory in the insert member, pressure is continually applied to all surfaces of the needle, thereby creating a firm grip on, and safely encapsulating, the needle. This is particularly advantageous because it substantially insures that the needle will not loosen or fall out if the device is tipped over or dropped. In fact, it has been found that a cross-link polyethylene material provides such a strong grip on the needle that the needle will remain implanted within the insert even if the transport device falls on the floor or is thrown against the wall. Thus, in order to remove the needle, it must be withdrawn manually by a deliberate force, thereby insuring that used needles are secured to permit safe transport to the place of ultimate disposal.

Advantageously, housing 52 may include abuttment indicated at 59 for helping retain the insert 54 in its proper location at the bottom of transport device 51. Alternatively, the insert can be retained by a tight friction fit and/or by adhering, such as by a hot melted glue to the inner walls of housing 52. Similarly, end cap 56 can be secured by a tight friction fit and/or by appropriate adhesive, as disclosed above. Weight 58 can, as disclosed above, be a metal insert, a threaded nut or a ceramic magnet.

As here embodied, a collar member (indicated generally at 60) may be installed at the open top end of housing 52 to provide the added feature of temporarily storing butterfly or like needles from an I.V. or blood collecting assembly. To this end, collar 60 includes an opening (indicated at 62) for receiving a used I.V. needle (indicated at 64 in FIG. 5). As here embodied, collar 62 also includes a top flange 61 to limit inward insertion of the collar and a conical, or inwardly tapered, skirt (indicated at 63) which is received within the open end of housing 52. It will be understood that by providing a tapered or conical skirt 63, room is provided between the outer surface of skirt 63 and the inner surface of housing 52 to receive and retain the needle.

As is apparent from FIG. 5, collar 60 may be secured to housing 52 by any convenient means apparent to those skilled in the art. As here embodied, the collar is secured by "punching" two or more half-moon shaped tabs (indicated at 52a and 63a) in both the wall of housing 52 and the skirt of collar 60, respectively. The tabs 52a are punched inwardly a distance at least beyond the skirt 63 so that they become an obstruction to prevent withdrawl of the collar from housing 52 and thereby lock it in place.

Advantageously, a removable top cap member (indicated at 66) may be included for covering the open top end of transport device 51. As here embodied, the top cap member 66 may be a snap-on lid which snaps over the radially outwardly projecting edges of flange 61. It will be understood by those skilled in the art that the top cap member permits complete enclosure of the transport device 51 to facilitate carrying the device when not being used to actually store a used needle. A tab (indicated at 66a) may be formed on the top cap member to aid in the removal of the cap when device 51 is to be used to receive a used needle. In addition, the bottom of housing 52 may be a slightly outwardly flared bottom (indicated at 52b) proportioned to likewise permit removable attachment of cap member 66. It will be understood that this provides a convenient way to store the cap member when device 51 is being used to store needles, yet makes it conveniently available for closing the top of device 51 after the contents of the device have been removed.

It will be understood by those skilled in the art that housing 52 should be proportioned to allow a needle to be inserted and withdrawn without requiring the user to reach inside the tube and thereby risk touching either the inside walls of the tube or any portion of the needle. In exemplary embodiment, the housing 52 can be from about three inches to about 5½ inches high and between about ¾ of an inch and one inch in diameter. However, variations in size can be made according to the anticipated use for the device—i.e., the expected size of the needles to be used with the device.

It will also be understood that the foam-like insert in the transport device according to the invention can be saturated with a disinfectant and or deodorant fluid. This further insures that the transport device according to the present invention can be safely resued several times. One such disinfectant is sold under the name "sporicidin" sold by Dentsply International, Inc. of York, Pa.

Figure 6:
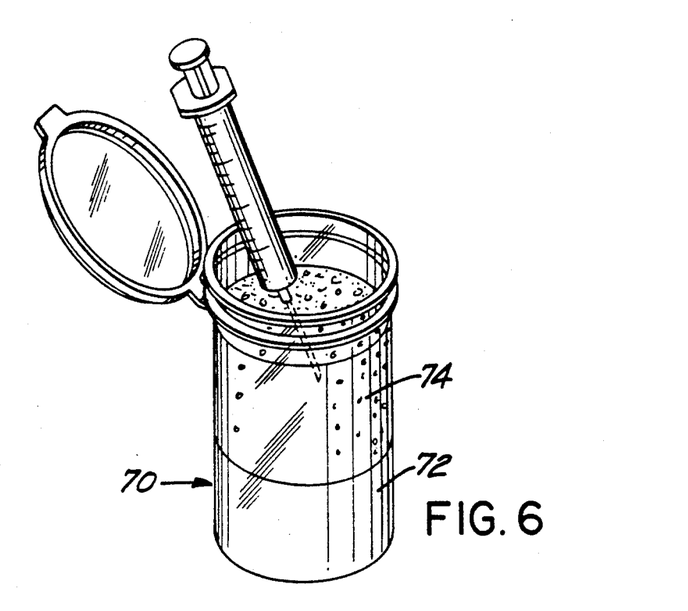
FIG. 6 is a front isometric view of still another preferred embodiment of a sharps transport device according to the present invention.
Figure 7:
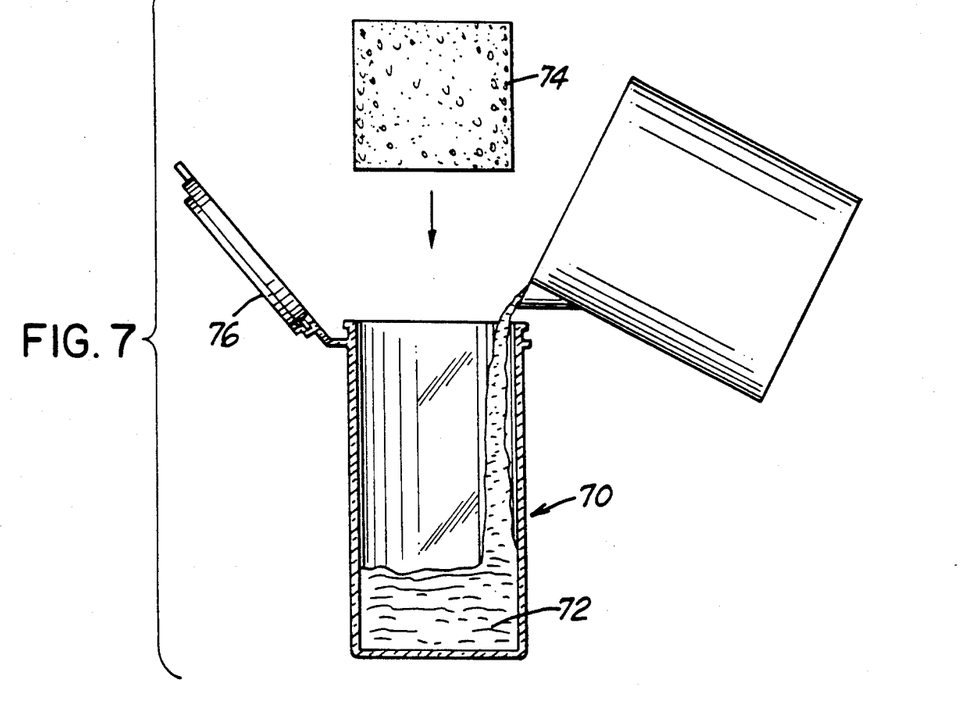
FIG. 7 is a front elevation view, in partial section, showing a method of fabricating the embodiment illustrated in FIG. 6.

Referring now to FIGS. 6 and 7, there is illustrated another preferred embodiment of sharps transport device according to the present invention. As here embodied, the housing, indicated at 70, is formed with an integral bottom. According to this aspect of the invention, the weighted bottom of the transport device is formed by pouring a cement-like composition, or other hardenable compound (indicated at 72), into the bottom of housing 70. Thereafter, the foam or rubber-like insert (here indicated at 74) on top of the hardenable material 72.

Depending on the composition used for the hardenable materials, the insert 74 may actually become adhered to the composition if it is inserted before the composition sets or hardens. Alternatively, the insert may simply be glued or otherwise adhered to the hardened composition after it has set. It has been found that by pouring a hardenable composition into a cup-like housing, fabrication of the complete transport device can be relatively simple and a relatively inexpensive material can be used. In addition, once the hardenable material sets, it will doubtlessly be automatically adhered to the housing.

Also as shown in FIGS. 6 and 7, the housing 70 includes a top cap cover permanently attached to the upper portion. As with top cover 66 described above, cap 76 can be used to cover the device when it is not being used to hold used needles.

It will be appreciated by those skilled in the art that the present invention in it broader aspects is not limited to the particular embodiments shown and described herein. Thus, it will be appreciated that the housing can be formed in any configuration to accommodate a desired number of implements. For example, in order to accommodate several "sharps", the housing can be oval or elliptical in shape—6" long×2" wide ×3" high. Accordingly, it will be understood that variations may be made which are within the scope of the accompanying claims without departing from the principle of the invention and without sacrificing its chief advantages.

What is claimed is:

1. A re-usable sharps storage/transport device for temporarily retaining used hypodermic needle/syringe assemblies intended for ultimate disposal, comprising a generally open-topped container proportioned to receive at least one needle/syringe assembly, in-tact, said container including a weight member generally at its bottom and a needle-piercing insert member generally above said weight member, wherein said weight member is formed by a hardenable compound poured into said container and said insert is adhered to said weight member to keep said insert member in place, said insert member comprising a material which has a memory, such that when said insert is pierced by a needle, it will tend to retain said needle to resist inadvertent removal of the used needle/syringe assembly from said container until the used needle/syringe assembly is removed by a user for appropriate disposal, yet said insert will substantially return to its original configuration after removal.

2. A re-usable sharps storage/transport device for temporarily retaining used hypodermic needles/syringe assemblies intended for ultimate disposal, comprising a generally open-topped container proportioned to receive at least one needle/syringe assembly, in-tact, said container including a weight member generally at its bottom and a needle-piercing insert member generally above said weight member, wherein said weight member is formed by a hardenable compound poured into said container, said insert comprising a material which has a memory, such that when said inset is pierced by a needle, it will tend to retain said needle to resist inadvertent removal of the used needle/syringe assembly from said container until the used needle/syringe assembly is removed by a user for appropriate disposal, yet said insert will substantially return to its original configuration after removal.

3. A device according to claim 1 wherein said needle engaging insert member is made from a material selected from the group comprising a sponge foam rubber or foam plastic.

4. A device according to claim 3 wherein said needle engaging insert member is made of a cross-link polyethylene.

5. A device according to claim 2 wherein said hardenable compound is a cement composition.

6. A device according to claim 2 wherein said hardenable compound comprises a relatively dense plastic material.

7. A device according to claim 1, further comprising a top cap member for covering the open top of said container until use is desired.

8. A device according to claim 2, further comprising a top cap member for covering the open top of said container until use is desired.

9. A device according to claim 2 wherein said needle engaging insert member is made from a material selected from the group comprising a sponge foam rubber or plastic.

10. A device according to claim 9 wherein said needle engaging inset member is made of a cross-link polyethylene.

* * * * *